(12) United States Patent
Redmond et al.

(10) Patent No.: US 7,928,102 B2
(45) Date of Patent: Apr. 19, 2011

(54) IRRADIATED COMPOSITIONS AND TREATMENT OF CANCERS WITH RADIATION IN COMBINATION WITH TAUROLIDINE AND/OR TAURULTAM

(75) Inventors: Paul H. Redmond, Wilton (IE); Rolf W. Pfirrmann, Weggis (CH)

(73) Assignee: Ed. Geistlich Soehne AG fuer Chemische Industrie, Wolhusen (CH)

( * ) Notice: Subject to any disclaimer, the term of this patent is extended or adjusted under 35 U.S.C. 154(b) by 289 days.

(21) Appl. No.: 12/159,875

(22) PCT Filed: Jan. 4, 2007

(86) PCT No.: PCT/IB2007/000022
§ 371 (c)(1),
(2), (4) Date: Sep. 24, 2008

(87) PCT Pub. No.: WO2007/077528
PCT Pub. Date: Jul. 12, 2007

(65) Prior Publication Data
US 2009/0156584 A1    Jun. 18, 2009

Related U.S. Application Data

(60) Provisional application No. 60/756,569, filed on Jan. 6, 2006, provisional application No. 60/763,909, filed on Feb. 1, 2006, provisional application No. 60/842,156, filed on Sep. 5, 2006.

(51) Int. Cl.
*A61K 31/54* (2006.01)
(52) U.S. Cl. .................................................. 514/222.5
(58) Field of Classification Search .............. 514/222.5
See application file for complete search history.

(56) References Cited

U.S. PATENT DOCUMENTS 5,819,748 A    10/1998    Pfirrmann

FOREIGN PATENT DOCUMENTS

| | | |
|---|---|---|
| EP | 1247524 A1 | 10/2002 |
| WO | 9934805 A1 | 7/1999 |
| WO | 0139763 A2 | 6/2001 |

OTHER PUBLICATIONS

International Search Report dated Apr. 11, 2007 (PCT/IB2007/000022).

*Primary Examiner* — Raymond J Henley, III
(74) *Attorney, Agent, or Firm* — Rothwell, Figg, Ernst & Manbeck, P.C.

(57) ABSTRACT

A composition formed by subjecting to ionizing radiation a combination containing a radiation-protective amount of PVP along with a solution, gel or adhesive including taurolidine, taurultam or a mixture thereof; or an aggregate including collagen-free crystals of taurolidine, taurultam or a mixture thereof.

14 Claims, No Drawings

US 7,928,102 B2

IRRADIATED COMPOSITIONS AND TREATMENT OF CANCERS WITH RADIATION IN COMBINATION WITH TAUROLIDINE AND/OR TAURULTAM

CROSS REFERENCE TO RELATED APPLICATION(S)

This application is a 35 U.S.C. §371 National Phase Entry Application from PCT/IB2007/000022, filed Jan. 4, 2007, and designating the United States. This application also claims the benefit of U.S. Patent Application No. 60/756,569, filed Jan. 6, 2006; Patent Application No. 60/763,909, filed Feb. 1, 2006; and Patent Application No. 60/842,156, filed Sep. 5, 2006, the disclosures of which are incorporated herein in its entirety by reference.

FIELD OF THE INVENTION

The invention relates to irradiated compositions, methods and treatment of cancer.

BACKGROUND OF THE INVENTION

Methylol transfer agents, such as the antibacterial and antitoxin drug taurolidine and the related product taurultam, have been shown to exert a modifying effect on the toxicity of tumor necrosis factor (TNF) which is used, inter alia, in the treatment of tumors. Furthermore, the action of methylol transfer agents has been shown to be selective in that the growth of normal cell-lines was not significantly inhibited.

Taurolidine acts by transferring three methylol groups at the site of action, taurultam being an intermediate metabolite which itself transfers a single methylol group with liberation of the very well tolerated compound taurinamide. Thus, the two compounds act by essentially the same mechanism. It should be noted that methylol transfer is to be contrasted with methyl transfer which is characteristic of many highly toxic anti-tumor drugs. Taurolidine and taurultam have low toxicity and are not cytotoxic against normal cells.

Programmed cell death is an evolutionary conserved biological principle in the regulation of cell numbers. Sensitive cells contain death receptors which are activated when the appropriate ligands are secreted from neighboring cells. A prominent system in programmed cell death is Fas-ligand mediated apoptosis. Fas, also known as CD 95/APO-1, is a cell surface receptor and a member of the tumor necrosis factor receptor superfamily which mediates apoptosis in sensitive cells upon oligomerization by the Fas-ligand (FasL).

Radiation has also been utilized for treatment of cancers. receptor and a member of the tumor necrosis factor receptor superfamily which mediates apoptosis in sensitive cells upon oligomerization by the Fas-ligand (FasL).

Radiation has also been utilized for treatment of cancers.

There remains a need in the art for improved medicaments and methods for treatment of cancers.

SUMMARY OF THE INVENTION

In accordance with one embodiment, the invention is a composition formed by subjecting to ionizing radiation a combination comprising a solution, gel or adhesive including taurolidine, taurultam or a mixture thereof, along with PVP; or an aggregate comprising collagen-free crystals of taurolidine, taurultam or a mixture thereof. The invention also relates to methods of forming such a composition, and use of such compositions in the treatment of cancer or other diseases.

DETAILED DESCRIPTION

According to one aspect, the present invention relates to treatment of cancers and tumors in a subject by administering to the subject a methylol transfer agent such as taurolidine and/or taurultam, in a combination therapy including administering to the subject a tumor-inhibiting amount of radiation.

The invention also relates to irradiated methylol transfer agents and methods of sterilizing methylol transfer agents by exposing methylol transfer agents to ionizing radiation. The methylol transfer agents may be crystalline, amorphous, or present in a liquid such as an aqueous solution containing PVP.

In some embodiments, the methyl transfer agent is taurolidine and/or taurultam, more preferably in a form of a composition comprising collagen-free taurolidine and/or taurultam crystals. In preferred embodiments, the radiation is X-ray (Roentgen) or gamma radiation.

According to one embodiment, the radiation is within a range of from about 0.01 Gy to about 100 kGy. For sterilization of taurolidine and/or taurultam crystals, preferred radiation amounts are within a range of about 0.1-100 kGy. In other embodiments, the radiation amounts are within a range of about 1-60 kGy, about 10-50 kGy or about 20-35 kGy.

It has surprisingly been found that crystals of taurolidine and/or taurultam have substantially identical characteristics and stability as compared to their non-radiated counterparts.

According to one embodiment, the present invention relates to the ability of methylol transfer agents, such as taurolidine and/or taurultam, to treat cancer in combination therapy with radiation. Both taurolidine and its congener taurultam enhance the apoptotic effect of Fas-ligand in cancer cells at drug concentrations which per se show practically no effect on cell viability.

In embodiments where the composition is a combination comprising a solution, gel or adhesive including taurolidine and/or taurultam, the combination further includes a radiation-protective amount of PVP. Compositions comprising taurolidine and/or taurultam along with PVP are disclosed in U.S. Pat. No. 6,080,397, incorporated herein by reference. The PVP may be present in the combination in amounts within a range of about 1-15% by weight, about 4-10% by weight, or about 5-6% by weight. The average molecular weight of the PVP present in the combination preferably is within a range of about 3,000-14,000 daltons. Preferably, the PVP present in the combination is substantially free of PVP having a molecular weight greater than about 50,000 daltons (e.g., less than 1% by weight of such PVP). In preferred embodiments, the average molecular weight of the PVP is between about 7,000-12,000 daltons, e.g., about 7,000-11,000 daltons, with a 10,000 dalton average molecular weight of PVP being most preferred. In preferred embodiments, the combination is a solution or gel containing taurolidine and/or taurultam and PVP. Such preferred combinations include taurolidine and/or taurultam at a concentration within a range of about 0.1-10% by weight, about 0.5-3% by weight, about 1-3% by weight or about 2% by weight.

In accordance with one embodiment, the composition is formed by subjecting to ionizing radiation an aggregate comprising collagen-free crystals of taurolidine and/or taurultam. In accordance with one embodiment, the crystal size may average between about 0.1-1,000 μm or about 1-500 μm. The crystals may be normal crystals or micronized crystals.

Micronized crystals may have an average particle size within about 1-10 µm, e.g., about 5 µm. Normal crystals may have a particle size within a range of about 100-500 µm, e.g., about 180-300 µm.

The invention also relates to a method of forming a composition as defined above, comprising subjecting a combination or aggregate as defined above to ionizing radiation.

The invention further relates to a method of treating cancer utilizing a composition as defined above.

According to one embodiment, a method of treating cancer comprises administering a solution, gel or adhesive including taurolidine and/or taurultam along with PVP, to a cancer patient. According to this embodiment, the cancer patient is further administered a tumor cell growth inhibiting or preventing amount of ionizing radiation while said solution, gel or adhesive is present in the patient. The combination comprising a solution, gel or adhesive may be administered first to the cancer patient in a tumor-inhibiting or preventing amount, followed by administration of tumor-inhibiting, preventing or destroying amounts of ionizing radiation. In other embodiments, the combination may be administered during radiation treatment. In other embodiments, the combination is administered before and during radiation treatment. In all of these embodiments, the combination may be administered after radiation treatment as well.

In some preferred embodiments, the combination is a solution or gel. In one preferred embodiment, the combination is a solution containing taurolidine and/or taurultam and PVP.

Radiation may be electromagnetic or particle radiation. Examples of particle radiation include alpha radiation, beta radiation and neutron radiation. In preferred embodiments, ionizing electromagnetic radiation is utilized. Particularly, preferred embodiments utilize ionizing X-ray radiation or ionizing gamma radiation. Preferred embodiments utilize ionizing radiation with a wavelength within a range from about $10^{-8}$ to about $10^{-14}$ m. X-ray radiation generally has a wavelength of from about $10^{-8}$ to about $10^{-11}$ m (i.e., within a range of about 10-0.01 nm). Gamma radiation generally has a wavelength within a range of about $10^{-11}$ to about $10^{-14}$ m.

In another embodiment, a method of treating cancer with a composition according to the invention comprises administering to a cancer patient collagen-free taurolidine and/or taurultam crystals which have been subjected to ionizing radiation. Preferably, the ionizing radiation is in the form of X-ray or gamma radiation. In certain embodiments, gamma-radiation is preferred. According to one embodiment, the irradiated crystals may be present in an adhesive composition. Preferably, the adhesive composition initially is in a liquid or semi-liquid state when it is applied and adhered to an area of tissue from which a tumor has been removed. After application, the adhesive preferably increases in viscosity or at least partially solidifies while adhering to the tissue. In preferred embodiments, the adhesive utilized is a fibrin sealant matrix (e.g., fibrin glue). Fibrin glue is a two-component system of separate solutions of fibrinogen and thrombin. When the two solutions are combined, the resultant mixture forms an adhesive. The taurolidine and/or taurultam crystals may be mixed with either or both of the fibrinogen and/or thrombin components, prior to combining the two to form the fibrin glue. In preferred embodiments, the taurolidine and/or taurultam crystals are mixed with the fibrinogen component, prior to mixture of the fibrinogen and thrombin components. The taurolidine and/or taurultam crystals may be subjected to ionizing radiation before and/or after addition of the crystals to one and/or both fibrin glue components, or after the fibrin glue components are admixed together.

In other embodiments, a solution or gel containing taurolidine and/or taurultam is substituted for or added with taurolidine and/or taurultam crystals in one or both of the fibrinogen and/or thrombin components of a fibrin sealing matrix as described above, prior to administration to a patient.

In further embodiments, ionizing radiation is administered to a cancer patient after administration to the patient of taurolidine and/or taurultam crystals which have been subjected to ionizing radiation.

Radiation treatment dosages when utilizing X-ray or gamma radiation may be within a range of about 0.01-100 Gy, within a range of about 0.1-80 Gy, within a range of about 1-10 Gy, within a range of 0.5-10 Gy or within a range of 1-5 Gy. Generally, multiple dosage administrations of radiation are administered to a patient over a course of treatment. Total dosages of radiation treatment over a complete course of treatment may be within a range of 1-100 Gy, or 10-70 Gy.

Methylol transfer agents include methylol-containing compounds such as taurolidine and taurultam, and their derivatives. The terms methylol transfer agents and methylol-containing compounds are sometimes used herein interchangeably. The compounds taurolidine and taurultam are disclosed in U.S. Pat. No. 5,210,083. Other suitable methylol-containing compounds may include taurinamide derivatives and urea derivatives. Examples of derivatives of taurolidine, taurultam, taurinamide and urea which may be useful in the present invention can be found in WO 01/39763A2. Particularly preferred methylol transfer agents for utilization in accordance with the present invention are taurolidine, taurultam, biologically active derivatives thereof and mixtures thereof.

Alternatively, the compound is a taurinamide derivative, or a urea derivative. Examples of derivatives of taurolidine, taurultam, taurinamide and urea which may be useful in the present invention can be found in WO 01/39763A2.

Other methylol-containing compounds which may be suitable include but are not limited to 1,3-dimethylol-5,5-dimethylhydantoin, hexamethylene tetramine, or noxythiolin. By derivative of taurolidine or taurultam is meant a sulfonamide compound which possesses at least 10% of the neoplastic activity of taurolidine or taurultam, respectively. A sulfonamide compound is one having a R2N—SO2R' formula. Derivatives of the compounds described herein may differ structurally from a reference compound, e.g., taurolidine or taurultam, but preferably retain at least 50% of the biological activity, e.g., induction of apoptotic cell death, of the reference compound. Preferably, a derivative has at least 75%, 85%, 95%, 99% or 100% of the biological activity of the reference compound. In some cases, the biological activity of the derivative may exceed the level of activity of the reference compound. Derivatives may also possess characteristics or activities not possessed by the reference compound. For example, a derivative may have reduced toxicity, prolonged clinical half-life, or improved ability to cross the blood-brain barrier.

While the invention herein is sometimes described in connection with taurolidine and/or taurultam, it is to be understood that other methylol transfer agents and methylol-containing compounds may be equally applicable.

The combination therapy of the invention includes administering tumor-inhibiting, tumor-reducing or tumor cell-killing amounts of radiation to the patient. As used herein, the term "tumor-inhibiting" is intended to include tumor-reducing and tumor cell-killing amounts. The radiation may be administered concurrently with or separately from the methylol transfer agent. The radiation may be administered in any effective amounts, e.g., within a range of from about 0.1-100

Gy or more, with preferred dosages within a range of about 0.1-5 Gy, most preferably within a dosage range of about 1-4 Gy per treatment. The radiation utilized may be any suitable tumor-inhibiting radiation, with roentgen radiation (X-ray) being preferred.

The methylol transfer agent and the radiation may be co-administered to a subject, or administered sequentially or cyclically.

In particularly preferred embodiments, a solution containing a methylol transfer agent such as taurolidine and/or taurultam, as well as containing PVP, is administered to treat cancer in a patient in combination therapy with radiation. In accordance with this embodiment, the PVP is at a concentration in the solution within a range of about 1-15% by weight. In preferred embodiments the PVP solution is in accordance with U.S. Pat. No. 6,080,397, incorporated herein by reference. In particularly preferred embodiments, the PVP in the solution has a weight average molecular weight in a range of from about 7,000-12,000 Daltons. One particularly preferred PVP is povidone. In preferred embodiments, the PVP is present in the solution in a range of about 4-10% by weight, most preferably about 5% by weight. A particular advantage of this embodiment is that a taurolidine and/or taurultam solution containing e.g. 5% povidone is stable against a radiation such as gamma-radiation. This is not the case if taurolidine and/or taurultam solution is used pure without povidone. PVP stabilises the taurolidine and/or taurultam solution against, e.g., oxidation caused by radiation. A patient who has been pre-treated with taurolidine and/or taurultam can be irradiated; radiation and taurolidine and/or taurultam can be administered simultaneously, subsequently treatment with taurolidine and/or taurultam can be continued. Because the solution is stable to radiation, one does not have to wait until the decomposition products are discharged from the patient.

In preferred embodiments, the method is carried out by administering to a mammal suffering from cancer, compositions containing an active methylol-containing compound, at a dose sufficient to induce death or growth reduction of neoplastic cells. By "methylol-containing compound," or "methylol transfer agent," is meant a compound which contains or is capable of producing a methylol molecule under physiological conditions. A methylol-containing compound is characterized as having a R—$CH_2$—OH group in which R is an alkyl, aryl or hetero group. The invention also includes the use of compounds capable of producing or being converted into a compound containing a R—$CH_2$—OH structure.

Cancers to which the present invention may be applicable include primary and secondary melanoma, glioma, neuroblastoma, astrocytoma, carcinomatous meningitis, ovarian cancer, prostate cancer, central nervous system (CNS) cancer, lung cancer, gastric cancer, esophageal cancer, urinary bladder cancer, leukemia, lymphoma, renal cell cancer, mesothelioma and metastases thereof. Other cancers against which the method of the present invention is effective include other primary and secondary carcinomas, sarcomas or lymphomas, cancers of the head and neck, liver cancer, breast cancer and pancreatic cancer, or their metastases.

Particularly preferred embodiments involve treatment of melanoma as well as metastases thereof.

It is particularly beneficial to use taurolidine and/or taurultam, at concentrations sufficient to induce apoptosis in cancer cells, to inhibit tumor cell growth, or to prevent the spread of metastases, especially following surgical removal of tumors. The mammalian subjects are typically humans.

The invention also includes the use of taurolidine and/or taurultam, at concentrations sufficient to induce apoptosis in cancer cells, and radiation for the treatment or prophylaxis of tumors in mammalian subjects.

Effective dosage amounts of a methylol transfer agent in accordance with the present invention may comprise pharmaceutical dosage units within the range of about 0.1-1,000 mg/kg subject body weight, preferably 150-450 mg/kg per day, and most preferably 300-450 mg/kg per day. Alternatively, the dosages can be administered on a grams/day basis, from about 2-60 g/day. Preferred doses may be in the range of about 2.5-30 g/day taurolidine, 4-60 g/day taurultam, or a mixture thereof. Most preferred doses are in the range of about 10-20 g/day taurolidine, 20-40 g/day taurultam, or a mixture thereof.

Suitable formulations for injection or infusion may comprise an isotonic solution containing one or more solubilizing agents, e.g., polyols such as glucose, in order to provide solutions of increased taurolidine or taurultam concentration. Such solutions are described in EP 253662B1. The concentration of taurolidine or taurultam in such solutions may be in the range 1-60 g/liter.

Methylol transfer agents are generally poorly soluble in water. Thus, it is often required to administer relatively large volumes of aqueous solutions containing taurolidine or taurultam, for example 10 g to 30 g of taurolidine and/or taurultam. Preferred solutions for administration in accordance with the present invention contain from about 0.5-2% taurolidine and/or taurultam. It may be convenient to administer these compounds by infusion in view of the relatively large volumes concerned, conveniently at intervals throughout the day.

Administration, preferably by infusion, of the total daily dose of methylol transfer agent can be carried out at a consistent rate over 24 hours, or according to a more rapid infusion schedule of the dose in portions, with breaks between each portion of the dose, e.g. infusion of 250 ml of a 2% taurolidine solution (5 g dose) over 2 hours, followed by a brief break of 4 hours, repeated over the course of a 24 hour infusion period to achieve a total daily dose of 20 g. Alternatively, 250 ml of a 2% taurolidine solution may be infused over one hour, with a one hour break between dose portions, and repeated until the daily dose is achieved, such that the total daily dose is provided over the course of less than 24 hours (i.e., approximately half the day), with no infusion occurring during the remainder of the day.

In accordance with one embodiment, four bottles (250 ml each) of 2% taurolidine solution are administered intravenously to patients with cancer, at a rate of 40 drops per minute, one bottle every six hours. The therapy cycle generally is an administration phase of daily infusions for one week, followed by a rest phase of two weeks. Total treatment generally is at least two such cycles. Efficacy of taurolidine 2% solution administered intravenously has been found to be particularly good with 25-28 bottles of 250 ml taurolidine 2% solution being instilled per cycle.

In accordance with a second embodiment of the invention, the administration phase comprises a daily regimen whereby 250 ml of taurolidine 2% solution is administered over the course of 2 hours, followed by a four hour break, repeated over 24 hours to achieve the total daily dose.

In accordance with a third embodiment of the invention, the administration phase comprises a daily regimen whereby 250 ml of 2% taurolidine solution is infused over one hour, followed by a one-hour break, and repeated until the daily dose is achieved. If the total dose is 20 g (for example), this regimen would provide the daily dose with four 250 ml infusions of 2% taurolidine over a 7 hour time span. No infusion occurs for the remainder of the day. Infusion rates can be lengthened (e.g., to 250 ml over go or 120 minutes) if the patient shows an elevated liver count.

In particularly preferred embodiments, patients are subjected to dosing cycles having an administration phase of at least 3 continuous days, and up to about 8 continuous days, each administration phase being followed by a non-administration phase of about 1 day to about 4 weeks, e.g., 1-14 days, or even 3, 4 or more weeks, during which the methylol-containing compound is not administered to the patient. During each administration phase, the methylol-containing compound is administered each day. For example, administration phases of 3, 4, 5, 6, 7 and/or 8 days can be utilized, and non-administration phases of 1, 2, 3, 4, 5, 6, 7, 8, 9, 10, 11, 12, 13, and/or 14 days may be utilized. At least 2 dosing cycles are utilized, preferably 5-10 or more dosing cycles are utilized. For example, 2, 3, 4, 5, 6, 7, 8, 9, 10 or more sequential dosing cycles can be utilized. Such a regimen has shown surprising and unexpected results with patients. In one particularly preferred embodiment, 6 dosing cycles, each with administration phases of 5 days are utilized, with each administration phase separated by a non-administration phase of 2 days. Preferably, during each day of administration, 250 ml of taurolidine 2% solution is intravenously administered to the patient 4 times daily.

In another embodiment, a non-administration phase may be 1, 2, 3, 4 or more weeks in length, e.g., about 2-4 weeks. For example, in patients with recurrent cancers such as of the stomach and pancreas may be administered sequential dosing cycles having an administration phase of 3-8 continuous days, e.g., 7 days, with, for example, 250 ml taurolidine 2% solution infused 4 times daily, followed by a non-administration phase of 1, 2, 3, 4, or more weeks, e.g., 3 weeks. As in the previous embodiments, at least 2 dosing cycles are utilized, preferably 5-10 or more dosing cycles.

The tumor-inhibiting radiation may be administered multiple times per day, once daily, once weekly, twice weekly, three times weekly, four times weekly, five times weekly, six times weekly, every two weeks, monthly, etc., or any suitable administration regimen. The radiation may be administered in dosing cycles as described herein with respect to the methylol transfer agent.

Fluid and electrolyte replacement may be administered in connection with intravenous taurolidine 2% therapy.

An amount of 250 ml of full electrolyte solution is preferably be given at the same time and with the same infusion speed parallel to the infusion with 250 ml taurolidine 2%. Electrolytes and blood count should be monitored twice per day, and the central vein pressure should be checked once daily.

If a hypernatraemia is observed, first, it should be determined whether dehydration is the cause. Diuretic agents should only be used if fluid is replaced at the same time and after dehydration was ruled out as the reason.

The methylol-containing compound is administered alone or in combination with one or more additional antineoplastic agents. In one preferred embodiment, the supplemental agent kills tumors cells by a mechanism other than apoptosis. For example, an antimetabolite, a purine or pyrimidine analogue, an alkylating agent, crosslinking agent (e.g., a platinum compound), and intercalating agent, and/or an antibiotic is administered in a combination therapy regimen. The supplemental drug is given before, after, or simultaneously with the methylol-containing agent. For example, the methylol transfer agent can be co-administered with a fluoro-pyrimidine, such as 5-fluoro-uracil (5-FU). Effective daily dosage amounts of a fluoro-pyrimidine may be in the range of about 0.1-1,000 mg per pharmaceutical dosage unit. Effective dosage amounts of 5-FU also may be in the range of about 100-5,000 mg/m2 body surface area, preferably about 200-1,000 mg/m2 body surface area, more preferably about 500-600 mg/m2 body surface area. 5-FU typically is provided in 250 mg or 500 mg ampules for injection, or 250 mg capsules for oral administration.

In another embodiment, the apoptotic effect of methylol transfer agents can be enhanced by co-administration with a Fas-ligand. A Fas-ligand polypeptide is disclosed in U.S. Pat. No. 5,858,990. Therapeutically effective amounts of Fas-ligand generally will be within a range of about 0.01-1,000 mg/kg patient body weight, preferably about 0.1-200 mg 1 kg patient body weight, most preferable about 0.2-20 mg/kg patient body weight. The therapeutically effective amounts can be administered as dosages once per day, or multiple times per day such as two, three, four or more times per day.

The invention also includes treating a drug resistant tumor, e.g., a multiple drug resistant (MDR) tumor, in a mammal by administering to the mammal a methylol-containing compound in conjunction with radiation. The drug resistant tumor is selected from the group consisting of a solid tumor, a non-solid tumor, and a lymphoma. For example, the drug resistant tumor may be a melanoma, breast cancer, ovarian cancer, colon cancer, prostate cancer, pancreatic cancer, CNS cancer, liver cancer, lung cancer, urinary bladder cancer, lymphoma, leukemia, or sarcoma.

According to another embodiment, a solution containing taurolidine and/or taurultam further contains taurin, in an amount within a range of about 1-20 g/l, preferably about 5 g/l.

A further embodiment provides methods for treating both primary liver tumors and metastases thereof, by direct administration of a solution containing a methylol transfer agent to the liver through a catheter installed in a hepatic vessel. By administering the methylol transfer agent in a solution that assists in maintaining liver function and non-ischemic conditions, therapy is directed to the affected organ, without unduly subjecting the organ to undue stress.

For treatment of primary liver tumors, the solution of methylol transfer agent may be administered through the hepatic artery, such that the therapeutic agent is carried into the organ for maximum effect. Alternatively, the solution can be supplied via the gastroduodenal artery, for delivery to the liver through the hepatic artery. The preferred solution for use in this embodiment is one that assists in maintaining liver function and minimizing stress to the organ associated with infusion of large volumes of methylol transfer agent solution.

Example 1

Isotonic Solution 2% Taurolidine

One suitable composition for intravenous drop infusion is shown below.
Isotonic sterile solution, 100 ml:
2.0 g Taurolidine
5.0 g PVP 16 PF UP aqua dest. ad solut. 100 ml. PH 7.2-7.3
Sterile-filtered and radiation sterilization.

Example 2

Isotonic Taurolin® Solution 2% Taurolidine with Taurin and Electrolytes

Another suitable composition for intravenous drop infusion is shown below.
Isotonic sterile solution, 100 ml:
2.0 g Taurolidine
5.0 g PVP 17 PF UP 0.5 g Taurin
0.3 g Sodium chloride
Sterile-filtered and radiation sterilization

Example 3

Isotonic Taurolin® Ringer Solution 2% Taurolidine with Taurin and Electrolytes

Another suitable composition for intravenous drop infusion is shown below.
Isotonic sterile solution, 100 ml:
2.0 g Taurolidine
5.0 g PVP 17 PF UP
0.5 g Taurin
0.26 g Sodium chloride
0.0033 g Potassium chloride
0.004 g Calcium chloride $2H_2O$
0.003 g Sodium hydrogen carbonate
Sterile-filtered and radiation sterilization

Example 4

Taurolin® Ringer-Lactate 2% Taurolidine with Taurin and Electrolytes

Another suitable composition for intravenous drop infusion is shown below.
Isotonic sterile solution, 100 ml:
2.0 g Taurolidine
5.0 g PVP 17 PF UP
0.5 g Taurin
0.20 g Sodium chloride
0.013 g Potassium chloride
0.009 g Calcium chloride $2H_2O$
0.0033 g Sodium lactate 50% solution (Pharmacopeia Europea)
Sterile-filtered and radiation sterilization

Example 5

Taurultam Solution

One preferred solution comprises:

| | |
|---|---|
| Lactobionic acid | 35.830 g |
| Adenosine | 1.340 g |
| Raffinose Pentahydrate | 17.830 g |
| Hydroxyethyl starch (HES) PL 40/0.5 | 50.000 g |
| Glutathione | 0.929 g |
| Allopurinol | 0.136 g |
| Taurultam | 10.000 g |
| Kcl | 5.200 g |
| $MgSo_4 7H_2O$ | 1.230 g |
| NaOH 25% GV to pH 7.8 | |
| NaOH pellets Merck 6482 | |
| Distilled water | 900 ml |

The solution is sterilized with radiation. The pH after sterilization is 7.2, and pH of ready to use solution is 7.47.

Example 6

Treatment of Melanoma

Melanoma is a form of skin cancer and its incidence increased sharply in recent years. Furthermore, malignant melanoma exhibits a poor response to radiotherapy and chemotherapy. This project was designed to evaluate the effect of taurolidine, a novel anti-neoplastic agent, alone or in combination with radiation, on melanoma tumour growth in vitro and in vivo.

Murine melanoma B16 4A5 and B16 F10 cells were treated with taurolidine (0-200 μg/ml), X-ray (Roentgen) radiation (0-4 Gy), or their combination for different time points. Cell cycle was assessed by FACScan analysis. Cell apoptosis and necrosis were determined by FACScan analysis and MTT assay, and further confirmed by DNA gel electrophoresis. Taurolidine alone arrested B16 4A5 and B16 F10 cell cycle at $G_0/G_1$ phase with an enhanced sub-$G_1$ population in a dose- and time-dependent manner. In contrast, the combination of taurolidine with radiation induced cell cycle arrest at $G_2/M$ phase with absence of sub-$G_1$ population. Exposure of B16 4A5 and B16 F10 cells to taurolidine 10-200 μg/ml resulted in a dose- and time-dependent cell apoptosis. Furthermore, 25 μg/ml taurolidine in combination with 0.5 Gy radiation led to a 70% apoptosis in B16 4A5 cells, whereas either of them alone failed to induce apoptosis.

C57BL/6 mice (8-10 week old) (n=120) were injected with B16 4A5 cells ($5 \times 10^5$ per mouse) into the right flank and divided into control, PVP (solvent for taurolidine), taurolidine (5 mg/mouse, i.p), radiation (5 Gy/mouse), and taurolidine plus radiation. Tumour growth rate, tumour/body weight ratio, lung metastases, and survival rate were recorded. Intratumour cell mitosis/apoptosis index, microvessel desity, and splenic cytotoxic T-lymphocyte (CTL) and nature killer (NK) cell-mediated cytotoxic activity were also accessed. Taurolidine plus radiation significantly attenuated primary and metastatic melanoma tumour growth when compared to untreated animals (p<0.001). Furthermore, mice treated with taurolidine plus radiation showed a greater reduction in tumour growth rate, tumour/body weight ratio, and lung metastatic nodules than mice treated with taurolidine alone (p<0.01) or radiation alone (p<0.01), which was mirrored by significant decreased cell mitosis/apoptosis index in the taurolidine plus radiation group. Mice treated with taurolidine plus radiation also demonstrated an improved survival and enhanced CTL and NK cell cytotoxic activity.

Taurolidine induces cell cycle arrest and apoptosis in two murine melanoma cell lines. In vivo taurolidine, when combined with radiation, significantly attenuates primary and metastatic melanoma tumour growth, which may result from taurolidine-induced cell apoptosis and enhanced radio-sensitivity.

Example 7

Two-Cycle Dosing Schedule for Treating Patients with Cancer Using Intravenous Taurolidine 2%

Four bottles (250 ml each) of 2% taurolidine solution are administered intravenously to patients with cancer, at a rate of 40 drops per minute, one bottle every six hours. The dosing cycle consists of an administration phase of daily infusions for one week, followed by a non-administration phase of two weeks, then followed by another administration phase of four bottles per day as previously indicated. Efficacy of taurolidine 2% solution administered intravenously has been found to be particularly good with 25-28 bottles of 250 ml taurolidine 2% solution being instilled per cycle.

Example 8

Four-Cycle Dosing Schedule for Treating Patients with Malignant Gliomas Using Intravenous Taurolidine 2%

The treatment comprises a minimum of 4 cycles. Each cycle is 7 days long, and is comprised as follows:

1. First Cycle
   a. Intravenous infusion of 250 ml taurolidine 2% and 250 ml full electrolyte solution via the central vein catheter with an infusion time of 60 minutes.
   b. If this therapy causes an elevated liver count, it is necessary to increase the infusion time to go or 120 minutes.
   c. 60-minute break
   d. Repeat the therapies under a or b and c for a total of 6 times per day.
   e. At an infusion time of 60 minutes the duration of the daily infusion program per 250 ml of taurolidine is 11 hours, at go minutes of infusion time 14 hours, and at 120 minutes of infusion time 17 hours. No drug is administered for the remainder of the time.
   f. rest phase
2. Subsequent Cycles
   a. Intravenous infusion of 250 ml taurolidine 2% and 250 ml full electrolyte solution via the central vein catheter with an infusion time of 60 minutes.
   b. If this therapy causes an elevated liver count, it is necessary to increase the infusion time to go or 120 minutes.
   c. 60 minute break
   d. Repeat the therapies under a or b and c for a total of 4 times per day.
   e. At an infusion time of 60 minutes the duration of the daily infusion program per 250 ml of taurolidine is 7 hours, at go minutes of infusion time 9 hours, and at 120 minutes of infusion time 11 hours. No drug is administered for the remainder of the time.

Example 9

Gamma Radiation and Taurolidine Treatment

Crystalline Taurolidine Powder
Average particle seize of normal crystals 180-300 μm
Average particle seize of micronised crystals=5 μm Two batches of normal crystalline taurolidine powder were produced and sterilised by gamma-radiation. The taurolidine crystals 0.5 g were weighed into 5 ml vials under sterile conditions and laminar flow. The vials were closed by rubber stoppers and seal caps. The closed vials were then radiated with gamma rays of 25 kGy (Range certification 26-30 kGy) and subsequently analysed.

Surprising result:

The evaluation of stability showed that the crystals of the taurolidine powder after sterilization by gamma radiation were identical with non-radiated crystals and corresponded to the specification of non-radiated crystals (Taurolidine standard) while 1% aqueous taurolidine solutions without PVP are not as stable to gamma radiation.

The following control evaluations have been done which demonstrate identical results from radiated and non-radiated crystalline taurolidine powder:

Melting point: 173-175° C.

IR-spectrum: Philips PU 9706 IR-spectrophotometer. The spectrophotogram corresponded to the non-radiated taurolidine standard.

Solubility: 1% clear solution in water.

Sterility: The compound was sterile according to Ph. Eur. 5.

Endotoxins: Test for endotoxins was negative.

Example 10

Approximately 0.5 g or more, depending on the size of the tumor cavity, of the taurolidine crystals as a suspension produced according to Example 9 are directly inserted into a two-component system fibrinogen/thrombin at a temperature of about 37° C. and locally lodged manually or by means of a spray device into a tumor cavity after surgical removal of a tumor. On an inner surface of the tumor cavity a fibrin adhesive matrix is formed which releases taurolidine by diffusion into the surface of the tumor cavity.

Alternatively, the crystals, preferably micronised taurolidine, can be filled into one chamber of a double chamber syringe, which contains fibrin glue in the other chamber and should subsequently mixed before use.

Example 11

Stability of Taurolidine Gel following Gamma Radiation

Introduction

In the present experiment, coarse granules of taurolidine gel, were exposed to gamma radiation twice at a maximum irradiation dose of 32 kGy each. The tauroline content was determined six fold before and after the second gamma irradiation by means of a selective HPLC method (Monograph for taurolidine gel, 4% taurolidine).

Results

| one-time irradiation | irradiation twice |
|---|---|
| 4.04 | 3.97 |
| 4.07 | 3.91 |
| 3.90 | 3.83 |
| 4.04 | 3.86 |
| 3.98 | 3.89 |
| 3.93 | 3.71 |

| F-TestTwo-Sample for Variances | | | t-Test: Two Sample Assuming Equal Variances | | |
|---|---|---|---|---|---|
| | Variable 1 | Variable 2 | | Variable 1 | Variable 2 |
| Mean | 3.9933 | 3.8616 | Mean | 3.9933 | 3.8616 |
| Variance | 0.0046266 | 0.0077766 | Variance | 0.0046266 | 0.0077766 |
| Observations | 6 | 6 | Observations | 6 | 6 |

| | | | | | |
|---|---|---|---|---|---|
| df | 5 | 5 | Pooled Variance | | 0.0062016 |
| F | 1.68083573 | | Hypothesized Mean Difference | | 0 |
| P (F <= f) one-tail | 0.29131282 | | df | | 10 |
| F Critical one-tail | 5.05033881 | | t stat | | 2.8958913 |
| | | | P (T <= t) one-tail | | 0.0079727 |
| | | | t Critical one-tail | | 1.8124615 |
| | | | P (T <= t) two-tail | | 0.0159454 |
| | | | t critical two-tail | | 2.2281392 |

Discussion

Even after two gamma irradiations with a maximum overall dose of 64 kGy, the taurolidine content is still within the specified release rate of 3.8 to 4.2%. It should be stressed that with normal gamma irradiation the maximum dose of 32 kGy is never exceeded and that the dose of 64 kGy selected for this experiment is by far higher; however, even when exposed to such a stress test, the active ingredient content does not drop below the lower release limits.

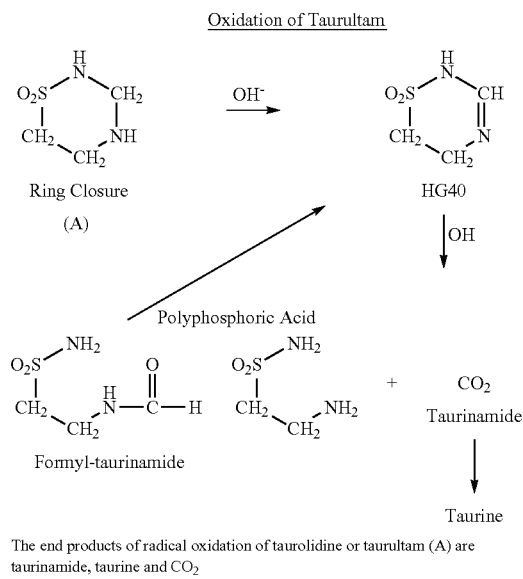

The end products of radical oxidation of taurolidine or taurultam (A) are taurinamide, taurine and $CO_2$ Determination of Dehydrotaurultam (HG 40)

After irradiation, the final W absorption of taurolidine 1% increased by 200-210 nm. In the process, a compound with an isolated double bond must have developed.

Mass Peak 135 (HPLC/MS)

At analysis of the residue from the mother liquors from the taurolidine crystallization by means of HPLC/MS, besides the taurultam, taurinamide and taurine mass peaks a mass peak of 135 (134) could be determined. This peak was identical to the peak of HG 40.

Synthesis of Dehydrotaurultam (HG 40)

By chemical reaction of the taurinamide base with formic acid, a good yield of N-formyl taurinamide develops. By heating it in polyphosphoric acid, dehydrotaurultam (HG 40) is obtained as a result of dehydration and ring closure. As an amidine, the substance contains an isolated C=N double bond.

Colorless platelets, recrystallized from alcohol, with a melting point of: 172-174° C. (Buechi melting point Apparatus 510).

Elemental Analysis

| | MG 134 | | | |
|---|---|---|---|---|
| Calculated: | C: 26.89 | H: 4.31 | N: 20.91 | S: 23.93% |
| Measured: | C: 27.05 | H: 4.54 | N: 20.5 | S: 23.79% |

Infrared Spectrum

In addition to the typical bands of taurultam, a new spectral band appears that corresponds to a C=N double bond.

NMR

The NMR analysis confirms the structure.

Through hydrolysis with HCl, HG 40 again turns into taurinamide.

Tautomeric Form of HG 40

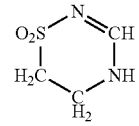

By rearranging the double bond, the tautomeric form of HG 40 is deduced.

Summary and Conclusion

Examination of an aqueous 1% taurolidine solution for radiolysis products. After γ-irradiation (approx. 25 gKy) of a 1% taurolidine solution contained in 500 ml glass bottles the following products can be isolated, or quantitatively determined by means of IR spectroscopy, HPLC/MS analysis, amino acid analysis:

| | | | |
|---|---|---|---|
| 1. | taurolidine content | 0.78% | 3,900 mg |
| 2. | dehydrotaurultam | 0.156% | 780 mg* |
| 3. | taurinamide | 0.0171% | 85.5 mg |
| 4. | taurine | 0.0106% | 53 mg |
| 5. | methylene glycol | 0.0160% | 81 mg** |
| 6. | $CO_2$ | 0.0019% | 9.7 mg |

*The content of dehydrotaurultam is estimated (HPLC/MS). It also contains the tautomeric form of HG 40.

The radical oxidation of taurolidine occurs analogously to the known oxidative cell biotransformation of taurolidine into taurinamide, taurine and $CO_2$. In this process, dehydrotaurultam develops as an intermediate product.

Example 12

Comparison of Acute Toxicity Between Taurultam and Dehydrotaurultam

Introduction

Provisions were made for sterilization of moist tauroline granules by means of gamma radiation. Besides the known products taurinamide and taurultam, traces of dehydrotaurultam were determined in the irradiated samples.

In the present report, the acute toxicity of dehydrotaurultam was evaluated compared to taurultam. For this, two different categories of cells (muscle cells and fibroblasts) were incubated with three different concentrations of the two test substances for different periods of time. A possible toxic effect of the test substances on the cells was analyzed 20 hours later. The measures to determine possible cell damage were viability and level of cell adhesion.

Samples

Taurultam, Geistlich Wolhusen, Batch E/39024/4 (powder)

Dehydrotaurultam, Geistlich Wolhusen, HG 40 batch Dec. 28, 1998/ib (powder)

Culture medium consisting of: DMEM (GIBCO BRL batch 10829), 10%

FBS (fetal bovine serum, GIBCO BRL) and 2 mM glutamine.

Cells: COS-7 fibroblasts and C2C12 myoblasts

Methods

Cell Culture:

The COS-7 and C2C12 cell lines were plated at 50% confluence on 48 well dishes, and incubated for 24 hours at 37°. Then the media were changed. To this, either unmodified medium (control), or medium containing 0.1%, 0.25% or 0.5% taurultam or dehydrotaurultam was used. The cell cultures were incubated at 37° for 5, 10, 20, 60 and 120 minutes, and then washed three times with fresh medium. After a further 20 hours in the incubator at 37°, the cells were evaluated.

Cell Viability:

Trypan blue stain allows identification of cell viability because trypan blue can penetrate damaged cells, but not intact ones.

Adhesion:

As a measure of viability, the extent of cell adhesion was evaluated microscopically.

Results

Influence of Taurultam and Dehydrotaurultam on the Cell Adhesion

Cell adhesion was analyzed after 20 hours of incubation with taurultam and dehydrotaurultam respectively.

Testing of Muscle Cells (Table 1)

Test Substances at 0.1% concentration:

Incubation periods of 5, 10 or 20 minutes showed no impairment of cell adhesion, neither with taurultam nor with dehydrotaurultam (100% cell adhesion). After incubation for 2 hours, cell damage could be observed with taurultam (60% cell adhesion), which, however, was much less pronounced with dehydrotaurultam (90% cell adhesion) (Table 1).

Test Substances at 0.25% concentration.

Even at this maximum concentration, incubation of up to 20 minutes did not show significant changes in cell adhesion. Only at incubation periods of 60 and 120 minutes impairment could be detected, which was more pronounced with taurultam (60-70% adhesion) than with dehydrotaurultam (80% adhesion) (Table 1).

Test Substances at 0.5% concentration:

Even at this maximum concentration, no significant impairment of the adhesive properties was found at an incubation period of up to 20 minutes. At longer incubation periods of 60-120 minutes clear adhesion related problems (50-60% adhesion) appeared, which, however, were not observed to this extent with dehydrotaurultam (80-90% adhesion) (Table 1).

Testing of Fibroblasts (Table 2)

Test Substances at 0.1% concentration:
a) With an incubation period of up to 20 minutes, cell adhesion was not significantly affected, neither with taurultam nor with dehydrotaurultam. At more extended incubation periods (60 and 120 minutes), however, limited adhesion was observed with taurultam, but was not detected with dehydrotaurultam (Table 2).
b) Test Substances at 0.25% concentration:
At this concentration, a change in adhesion only occurred at an incubation period of at least 20 minutes. However, the adhesion related problems were much more pronounced with taurultam, (60% adhesion) than with dehydrotaurultam (80% adhesion) (Table 2).
c) Test Substances at 0.5% concentration:
At highest concentration, an incubation period of 10 minutes was practically ineffective. However, at more extended incubation periods considerable cell adhesion impairment occurred with taurultam (down to 40% adhesion); this effect was much less pronounced with dehydrotaurultam (80% adhesion) (Table 2).

Influence of Taurultam and Dehydrotaurultam on Cell Viability

The viability test of the adherent cells with trypan blue showed that in each group cell viability was greater than 95%. These findings were independent of the incubation period, the concentrations of the test substances or the test substance used. This means that practically all cells that maintain their adherent properties are fully viable. On the other hand, impaired cells lose their adherent characteristics. These findings support the validity of the adhesion test described above as a sensitive method to measure cell damage.

Discussion

Validity of the Test Methods

The viability tests with trypan blue showed that all adherent cells were fully viable. These findings demonstrate that adhesion is a sensitive marker for impaired cell viability. The adhesion test is designed to conduct further cell incubation for 20 hours subsequent to incubation with the test substances. As a result, the adhesion test not only provides information about the immediate effect of the test substances, but also includes cell damage that may develop as a result of one-time exposure.

Comparison of Cell Types

The maximum effect of taurultam and dehydrotaurultam on the adhesion of fibroblasts and of muscle cells are practically identical (Tables 1 and 2, maximum concentrations, and incubation period of 120 minutes). These findings allow the assumption that other cells also react to taurultam or dehydrotaurultam in a similar way.

Comparison of the Effects of Taurultam and Dehydrotaurultam

At an incubation period of 20 minutes, no considerable cell adhesion interference occurs in muscle cells, even at highest concentration (0.5%) of taurultam and dehydrotaurultam. Only after an incubation period of 60-120 minutes cell changes occur, which are less pronounced with dehydrotaurultam than with taurultam at all concentrations. Adhesion with dehydrotaurultam is 80-90% compared to 50-60% with taurultam at a 2-hour incubation period. A similar difference with respect to toxicity of dehydrotaurultam and taurultam was found with fibroblasts. While an incubation period of up to 10 minutes produced no changes even at highest concentration, longer exposure times (60-120 minutes) resulted in cell changes, which were considerably less pronounced with dehydrotaurultam at all concentrations than with taurultam.

Even under most extreme conditions (0.5%, 1-2 h), adhesion with dehydrotaurultam did not drop below 80%, while adhesion with taurultam was only 40-60%.

Summary

Comparative analysis of the effects of taurultam and dehydrotaurultam on the viability of muscle cells and fibroblasts revealed in a time- and concentration-dependent study that both substances exhibited very low toxicity. During acute exposure to the test substances no cell changes were observed. Cell damage was only detected at extended incubation periods. It is remarkable that at all tested concentrations and incubation periods dehydrotaurultam has a significantly lower toxic effect than taurultam (Tables 1, 2).

In moist tauroline granules exposed to gamma radiation dehydrotaurultam is present in very small amounts compared to taurultam. Therewith it can be assumed that dehydrotaurultam does not increase the toxicity risk of moist tauroline granules in humans.

Legend

Table 1

Muscle cells were incubated with taurultam or dehydrotaurultam (0.1%, 0.25%, 0.5%) for 5, 10, 20, 60 and 120 minutes at 37°. After rinsing them three times with a regular medium, the cultures were incubated for another 20 h. Then the extent of cells adhesion was examined microscopically. The results are shown in % of the control cultures. The adhering cells were viable.

Table 2

Fibroblasts were incubated with taurultam or dehydrotaurultam (0.1%, 0.25%, 0.5%) for 5, 10, 20, 60 and 120 minutes at 37°. After rinsing them three times with a regular medium, the cultures were incubated for another 20 h. Then the extent of adhesion of the cells was examined microscopically. The results are shown in % of the control cultures. The adhering cells were viable.

The invention claimed is:

1. A composition formed by subjecting to ionizing radiation a combination comprising a solution, gel or adhesive containing a radiation-protective amount of PVP and further including taurolidine, taurultam or a mixture thereof; or an aggregate comprising collagen-free crystals of taurolidine, taurultam or a mixture thereof.

2. The composition of claim 1 wherein said radiation is at a level of from about 0.01 Gy to about 100 kGy.

3. The composition of claim 2 wherein said radiation is X-ray or gamma radiation.

4. The composition of claim 3 wherein said composition comprises said combination comprising said PVP and said solution, gel or adhesive including said taurolidine, taurultam or a mixture thereof, wherein said radiation is at a level within about 0.01-100 Gy, said taurolidine, taurultam or mixture thereof is present in said combination in an amount of from about 0.1-10% by weight, said PVP has an average molecular weight of from about 3,000-14,000 daltons, and said PVP is present in said combination in an amount of about 1-15% by weight.

5. The composition of claim 3 comprising said aggregate comprising collagen-free crystals of taurolidine, taurultam or a mixture thereof, wherein said radiation is at a level of about 0.1-100 kGy, and said crystals have an average crystal size within a range of about 0.1-1000 μm.

6. A method of forming the composition of claim 1, comprising subjecting said combination or said aggregate to ionizing radiation.

7. The method of claim 6 wherein said ionizing radiation is X-ray or gamma radiation.

8. The method of claim 7 wherein said radiation is at a level of from about 0.01 Gy to about 100 kGy.

9. A method of treatment for treating tumor growth with a composition according to claim 1, comprising administering said solution, gel or adhesive containing said radiation-protective amount of PVP and including taurolidine, taurultam or a mixture thereof to a cancer patient, and administering a

TABLE 1

Influence of Taurultam and Dehydrotaurultam on the Adhesion of C2C12 Muscle Myoblast Cells

| Incubation Period in Minutes | Control | Taurultam 0.1% | Dehydrotaurultam 0.1% | Taurultam 0.25% | Dehydrotaurultam 0.25% | Taurultam 0.5% | Dehydrotaurultam 0.5% |
|---|---|---|---|---|---|---|---|
| 5 | 100% | 100% | 100% | 100% | 100% | 95% | 100% |
| 10 | 100% | 100% | 100% | 95% | 100% | 90% | 100% |
| 20 | 100% | 100% | 100% | 90% | 90% | 90% | 90% |
| 60 | 100% | 90% | 100% | 70% | 80% | 60% | 90% |
| 120 | 100% | 60% | 90% | 60% | 80% | 50% | 80% |

TABLE 2

Influence of Taurultam and Dehydrotaurultam on the Adhesion of COS-7 Fibroblasts

| Incubation Period in Minutes | Control | Taurultam 0.1% | Dehydrotaurultam 0.1% | Taurultam 0.25% | Dehydrotaurultam 0.25% | Taurultam 0.5% | Dehydrotaurultam 0.5% |
|---|---|---|---|---|---|---|---|
| 5 | 100% | 100% | 100% | 95% | 100% | 95% | 100% |
| 10 | 100% | 100% | 100% | 90% | 100% | 90% | 95% |
| 20 | 100% | 90% | 100% | 60% | 90% | 70% | 90% |
| 60 | 100% | 80% | 100% | 60% | 90% | 60% | 80% |
| 120 | 100% | 70% | 90% | 70% | 80% | 40% | 80% | tumor growth-inhibiting amount of ionizing radiation to said patient while said solution, gel or adhesive is present in said patient, said tumor being selected from the group consisting of primary melanoma, secondary melanoma, glioma, neuroblastoma, astrocytoma, carcinomatous meningitis, ovarian cancer, prostate cancer, central nervous system (CNS) cancer, lung cancer, gastric cancer, esophageal cancer, urinary bladder cancer, leukemia, lymphoma, renal cell cancer, mesothelioma, primary carcinoma, secondary carcinoma, sarcoma, or lymphoma, cancer of a head, cancer of a neck, liver cancer, breast cancer, pancreatic cancer, and metastases thereof.

10. The method of claim 9 wherein said solution, gel or adhesive is administered to said patient first, followed by administration to said patient of said ionizing radiation.

11. The method of claim 9 wherein said solution or gel is administered to said patient, and said solution or gel is administered to said patient during administration of radiation to said patient.

12. The method of claim 11, further including a step in which said solution or gel is administered before administration of said radiation to said patient.

13. A method of treatment for treating tumor growth in a patient, comprising administration to said patient a composition according to claim 1, the composition comprising said aggregate comprising collagen-free crystals of taurolidine, taurultam or a mixture thereof, wherein said aggregate is subjected to said ionizing radiation during a time period which is at least one of before, during or after administration of said aggregate to said patient.

14. A method of preparation of a composition for treating tumor growth in a patient, the method comprising subjecting to ionizing radiation a combination containing a radiation-protective amount of PVP and taurolidine, taurultam or a mixture thereof; or an aggregate comprising collagen-free crystals of taurolidine, taurultam or a mixture thereof; so as to form said composition.

* * * * *